United States Patent
Demo et al.

(10) Patent No.: US 7,005,254 B2
(45) Date of Patent: Feb. 28, 2006

(54) LETM1: MODULATORS OF CELLULAR PROLIFERATION

(75) Inventors: Susan Demo, Sunnyvale, CA (US); Yasumichi Hitoshi, Mountain View, CA (US); Denise Pearsall, Belmont, CA (US)

(73) Assignee: Rigel Pharmaceuticals, Incorporated, South San Franicsco, CA (US)

( * ) Notice: Subject to any disclaimer, the term of this patent is extended or adjusted under 35 U.S.C. 154(b) by 361 days.

(21) Appl. No.: 10/160,663

(22) Filed: May 31, 2002

(65) Prior Publication Data

US 2003/0040001 A1 Feb. 27, 2003

Related U.S. Application Data

(60) Provisional application No. 60/347,970, filed on Oct. 19, 2001, provisional application No. 60/296,817, filed on Jun. 7, 2001.

(51) Int. Cl.
*C12Q 1/00* (2006.01)
*C12Q 1/68* (2006.01)
*G01N 33/53* (2006.01)

(52) U.S. Cl. .................. 435/4; 435/6; 435/7.1
(58) Field of Classification Search ............ 435/4, 435/7.1, 6; 514/1
See application file for complete search history.

(56) References Cited

U.S. PATENT DOCUMENTS

2002/0132753 A1 * 9/2002 Rosen et al. .............. 514/1

OTHER PUBLICATIONS

Endele, et al.; "LETM1, A Novel Gene Encoding a Putative EF-Hand $Ca^{2+}$-Binding Protein, Flanks the Wolf-Hirschhorn Syndrome (WHS) Critical Region and Is Deleted in Most WHS Patents", Genomics 60, 218-225 (1999).
Database GenBank, Accession No. AF061025, Oct. 5, 1999.

* cited by examiner

*Primary Examiner*—Gary B. Nickol
(74) *Attorney, Agent, or Firm*—Townsend and Townsend and Crew LLP

(57) ABSTRACT

The present invention relates to regulation of cellular proliferation. More particularly, the present invention is directed to nucleic acids encoding LETM1 ("leucine zipper EF hand transmembrane receptor"), which is involved in modulation of cellular proliferation and cell cycle regulation. The invention further relates to methods for identifying and using agents, including small molecule chemical compositions, antibodies, siRNA, antisense nucleic acids, and ribozymes, that modulate cell cycle regulation and cellular proliferation via modulation of LETM1 and LETM1 related signal transduction; as well as to the use of expression profiles and compositions in diagnosis and therapy related to cell cycle regulation and modulation of cellular proliferation.

29 Claims, 10 Drawing Sheets

FIGURE 1

SEQ ID NO:1--NM_012318

```
   1 GAACCGGTAG TCCGCGGTGG CGCGGTCCGC CCCTCACCTG GCCAGCGGCG GGCGCTGAGG
  61 GGCCCAATGG GAGCCGCGGC CTGGCCGCCC CGCCCCGCGC CTCCGGACGT CTGTGCCGGG
 121 ACAAGGCCGC CGCTGGTGCC GGGTCCTTGA GGAGAGCGCC TCCCGTCCGA GGCCAGCCGC
 181 CTCTGTCAGC CGTCCGCGCG GGCCGGGTCT GAAGCGCCGC CGGGACGGCG AAGAGCCGCG
 241 GCCGCCGCGG AGAAGGAGGC AGCGCAGGAG GCCGGAGCGG CCGCCGCGCC CGAGCACATG
 301 GCGTCCATCT TACTGAGGAG CTGCCGCGGC CGGGCGCCCG CCCGCCTCCC GCCGCCGCCT
 361 CGGTACACCG TCCCGCGGGG TAGTCCAGGG GATCCTGCTC ATCTCAGCTG TGCCAGCACC
 421 CTGGGGTTGA GGAACTGCCT GAATGTTCCA TTTGGCTGCT GCACTCCCAT CCACCCTGTG
 481 TACACATCCT CCAGAGGCGA TCACCTCGGC TGTTGGGCTC TGAGGCCCGA GTGCCTTCGC
 541 ATAGTGTCGA GAGCGCCATG GACCTCTACC TCTGTGGGTT TTGTGGCTGT GGGACCTCAG
 601 TGCCTTCCTG TGCGTGGCTG GCACTCTTCG CGCCCTGTTC GCGATGACTC GGTAGTAGAG
 661 AAGTCCCTCA AGTCCTTGAA GGACAAGAAC AAGAAGCTGG AGGAAGGCGG CCCGGTGTAC
 721 AGCCCCCCCG CAGAGGTGGT GGTGAAGAAG TCCCTGGGGC AGCGGGTGCT GGACGAGCTG
 781 AAGCACTACT ACCATGGCTT CCGCCTGCTA TGGATCGACA CCAAGATCGC GGCACGCATG
 841 CTCTGGCGCA TCCTCAACGG CCACAGCCTG ACCCGCCGGG AGCGCAGGCA GTTTCTCCGG
 901 ATCTGCGCTG ACCTCTTCCG CCTGGTGCCG TTCCTTGTGT TCGTGGTGGT GCCGTTCATG
 961 GAGTTTCTGC TGCCTGTTGC TGTGAAGCTC TTCCCCAACA TGTTGCCATC CACATTTGAG
1021 ACTCAGTCAC TCAAGGAGGA GAGGCTGAAG AAGGAGCTTC GGGTCAAGCT GGAGCTGGCC
1081 AAGTTCCTCC AGGACACCAT CGAGGAGATG GCCTTGAAGA CAAGGCAGC CAAGGGCAGC
1141 GCCACCAAAG ACTTCTCTGT GTTTTTCCAG AAGATCCGGG AAACAGGGGA GAGGCCCAGC
1201 AATGAGGAAA TCATGCGTTT TTCCAAATTA TTTGAGGATG AGCTGACCCT GGACAACCTG
1261 ACACGGCCGC AGCTGGTGGC CCTGTGCAAG CTGCTGGAGC TACAGTCCAT CGGCACCAAC
1321 AACTTCCTGC GCTTCCAGCT TACCATGCGG CTGCGCTCCA TAAAGGCAGA CGACAAGCTG
1381 ATTGCTGAGG AAGGGGTGGA CAGCCTGAAT GTCAAGGAGC TGCAGGCAGC GTGTCGGGCA
1441 CGAGGCATGC GGGCCCTGGG CGTCACGGAA GACCGCCTGA GGGGTCAGCT GAAGCAGTGG
1501 CTGGACCTGC ACCTGCATCA GGAGATCCCC ACATCGCTGC TCATCCTGTC CGGGCCATG
1561 TACCTCCCGG ACACCCTCTC TCCAGCCGAC CAGCTCAAGT CCACACTGCA GACCCTCCCA
1621 GAGATTGTGG CAAAGGAAGC ACAGGTGAAA GTGGCCGAGG TGGAGGGCGA GCAGTGGAC
1681 AACAAGGCCA AGCTGGAGGC CACGCTGCAG GAGGAGGCGG CCATCCAGCA GGAGCACCGT
1741 GAGAAGGAGC TGCAGAAGCG CTCGGAGGTG GCGAAGGATT TGAGCCCGA ACGTGTGGTA
1801 GCTGCTCCCC AAAGGCCGGG GACCGAGCCA CAGCCAGAAA TGCCTGACAC AGTCCTGCAG
1861 TCAGAGACCT TGAAGGACAC TGCCCCGGTG CTGGAGGGCT TGAAGGAGGA AGAGATCACG
1921 AAGGAGGAAA TCGACATCCT CAGCGATGCC TGCTCTAAGC TGCAGGAGCA GAAGAAGTCA
1981 CTCACCAAGG AGAAGGAGGA GCTGGAGCTG CTGAAGGAGG ATGTGCAGGA CTACAGCGAG
2041 GACTTGCAGG AGATCAAGAA GGAACTTTCA AAGACTGGTG AAGAAAAATA CGTGGAAGAA
2101 TCTAAAGCCA GCAAGAGATT GACAAAAAGG GTGCAGCAAA TGATCGGGCA GATCGATGGC
2161 TTGATCTCGC AGCTGGAGAT GGACCAGCAG GCTGGCAAGC TGGCCCCGGC CAACGGCATG
2221 CCCACGGGGG AGAACGTCAT CAGTGTCGCT GCCGCAGCAC TGGATGAAAA CAAGGATGGC
2281 CACATTCCCG AAAGCAAGCT CACCAGCCTG GCCGCAGCAC TGGATGAAAA CAAGGATGGC
2341 AAGGTCAACA TCGACGACCT CGTCAAGGTG ATTGAGCTGG TGGACAAAGA AGATGTTCAC
2401 ATCTCCACCA GCCAGGTGGC TGAGATTGTA GCAACACTGG AAAAAGAGGA GAAGGTGGAG
2461 GAGAAGGAGA AGGCCAAAGA GAAGGCAGAG AAGGAGGTCG CAGAGGTGAA GAGCTAGAAC
2521 CACTGGCCTG GCACCTGTC CTCCTGCTGT GCCGTCACCC TGGCAAGGGC CGTGAGGGCG
2581 ATTGCTTTGT GGTGATTCTC AGTGGCTCAT CTAATATTTT GGCTGGAATA AATCAGAGAC
2641 TTCCATAATC AAGTAAATTT TAATTTTCAT CATTCCATGG AGATTCAGTC TGTCTGGAAT
2701 CCCGGAACCC CTCCACAGAA TCGTGTCTGG ATCCACACTG TGGTGTGGCT GCCACGGCCT
2761 CCTGGCTCCA GAGGCAGCTG GGCCGGGCCA AGGCAGGAAG GCGCCCCAT GTGTGTGGCC
2821 TCAGTCTCAG CATCTGACTG TGCTGCCCTG TCCCCAGGGA AGAGAATGAG GACCACGTGG
2881 ACTCCGCCCA CACAGAGCTG GCTGCTGTGC CCACCCTCAG GGCGTCAGG AGACACAGCC
2941 TGGCCTCCTC AGGGCTGAAG ATGCCTCCAT TCGCCTGTGG ACCTTGATTT CTAGATTTCA
3001 GTGTCAATAG ACCTGTCTTC CTGCACACTT TCAGTTGGAT GTGGGTCATT GTGGAGACAG
3061 AGGTGTCTGC CATCTCTGTG GCCTCTGGAG AGTGACGTCT CCCTGCTGGG AGTGCTGGTT
3121 CTCACGTGCG GTTTCCCTTG TGTATCGGAG CTCTTTCTCG GCTTTCTATT TCCCCCAGTT
3181 CTTTAAGCAG TCAATTGGCA CAGAGTTTCC CACGGGGCT GCAGTGGATT CACTGTGTCA
3241 GGGATGAGCC TGGCTTGGGG GTTGGTGGGG CTCTGAAGCG CATTTGGGGT TCTTTGTAGC
3301 TTCTAATGTG AGGTTTGAGT CCAGTGCGCC CACAGCAGCA TGCCCTTCTC ACCCCTTGCA
```

FIG. 1, page 1 of 2

```
3361 GTGTTGCAGG CTCAGGCCCC TGGGCTCCTT CAGCAAGCAG GCTAGTCAAT GAGGCATGAG
3421 GATCCGGCAC AGGGCATCCC CTGGGGCTTC AAGGGCAATA CCCCCGTGCT TAGGGTTTGC
3481 CCTGTGCCCT CTGGGTGGGG TGGCCTCCCC GCACTCGGCA GCATGGCCAG GCTGGCCAGG
3541 GCGTGGGCAG GTGGTGTCCT GTGGCACCTC CATCCTCCTG CCCAGCCGGC TGTGTCACAC
3601 TCATCTTTTT AAGGTCAGGT TGGTTCCTGG CAAAAATGTA CCTCCAGGGG CCTCCAAGCA
3661 TAGGATTTGG AAGACAGGAA CGGCACAGGC GTCCAGGAAA GCAGCTGCAC TCAGACAATG
3721 CCTTCTCCAT TACTTGAAGC TTCTTTCTGT TCAGCCATTA AAGAAACTTG ACAAAATAGG
3781 AACAGGAGAT ATTTCTCAAT TGTAAACCTT TGTGCAGGGA CAGTTGGCTT CCAGAGGTTT
3841 CAGCTTTCAG TTATTTGAGA AGTTTGTTTT AGATCCTTAA CTAATATTTA TGAATTCTCT
```

SEQ ID NO:2--NP_036450

```
    MASILLRSCR GRAPARLPPP PRYTVPRGSP GDPAHLSCAS TLGLRNCLNV PFGCCTPIHP
 61 VYTSSRGDHL GCWALRPECL RIVSRAPWTS TSVGFVAVGP QCLPVRGWHS SRPVRDDSVV
121 EKSLKSLKDK NKKLEEGGPV YSPPAEVVVK KSLGQRVLDE LKHYYHGFRL LWIDTKIAAR
181 MLWRILNGHS LTRRERRQFL RICADLFRLV PFLVFVVVPF MEFLLPVAVK LFPNMLPSTF
241 ETQSLKEERL KKELRVKLEL AKFLQDTIEE MALKNKAAKG SATKDFSVFF QKIRETGERP
301 SNEEIMRFSK LFEDELTLDN LTRPQLVALC KLLELQSIGT NNFLRFQLTM RLRSIKADDK
361 LIAEEGVDSL NVKELQAACR ARGMRALGVT EDRLRGQLKQ WLDLHLHQEI PTSLLILSRA
421 MYLPDTLSPA DQLKSTLQTL PEIVAKEAQV KVAEVEGEQV DNKAKLEATL QEEAAIQQEH
481 REKELQKRSE VAKDFEPERV VAAPQRPGTE PQPEMPDTVL QSETLKDTAP VLEGLKEEEI
541 TKEEIDILSD ACSKLQEQKK SLTKEKEELE LLKEDVQDYS EDLQEIKKEL SKTGEEKYVE
601 ESKASKRLTK RVQQMIGQID GLISQLEMDQ QAGKLAPANG MPTGENVISV AELINAMKQV
661 KHIPESKLTS LAAALDENKD GKVNIDDLVK VIELVDKEDV HISTSQVAEI VATLEKEEKV
721 EEKEKAKEKA EKEVAEVKS
```

FIG. 1, page 2 of 2

GENES CAUSING CELL CYCLE ARREST: ALAMAR
RATIO OF POSITIVE CLONES

| CLONES | GROWTH RATIO AT DAY 7 | | |
|---|---|---|---|
| | Exp-1 | Exp-2 | Exp-3 |
| GFP-p21(C20) | 2.3 | 3.3 | 3.4 |
| A2-11 | 1.2 | 1.0 | 0.8 |
| A3-2064 | 1.5 | 1.9 | 2.0 |
| A4-976 | 6.2 | 3.3 | 4.5 |

*FIG. 2.*

LETM1: MODULATORS OF CELLULAR PROLIFERATION

CROSS-REFERENCES TO RELATED APPLICATION

The present application is related to U.S. Pat. No. 60/296,817, filed Jun. 7, 2001, and U.S. Pat. No. 60/347,970, filed Oct. 19, 2001, herein each incorporated by referenced in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of cellular proliferation. More particularly, the present invention is directed to nucleic acids encoding LETM1 ("leucine zipper EF hand transmembrane receptor"), which is involved in modulation of cellular proliferation and cell cycle regulation. The invention further relates to methods for identifying and using agents, including small molecule chemical compositions, antibodies, siRNA, antisense nucleic acids, and ribozymes, that modulate cell cycle regulation and cellular proliferation via modulation of LETM1 and LETM1 related signal transduction; as well as to the use of expression profiles and compositions in diagnosis and therapy related to cell cycle regulation and modulation of cellular proliferation.

BACKGROUND OF THE INVENTION

Cell cycle regulation plays a critical role in neoplastic disease, as well as disease caused by non-cancerous, pathologically proliferating cells. Identifying membrane proteins, their ligands, and downstream signal transduction pathways is important for developing therapeutic regents to treat cancer and other proliferative diseases.

In recent years, there have been major developments in the understanding of the cell cycle. Normal cell proliferation is tightly regulated by the activation and deactivation of a series of proteins that constitute the cell cycle machinery. The expression and activity of components of the cell cycle can be altered during the development of a variety of human disease such as cancer, cardiovascular disease, psoriasis, etc., where aberrant proliferation contributes to the pathology of the illness. There are genetic screens to isolate critical components for cell cycle regulation using different organisms such as yeast, worms, flies etc., since cell cycle regulation is the most common machinery among all eukaryotic cells. However, there is a need to establish screening for understanding human diseases caused by disruption of cell cycle regulation and for the development of new therapeutics.

SUMMARY OF THE INVENTION

The present invention therefore provides nucleic acids encoding LETM1, which is involved in modulation of cell cycle regulation and cellular proliferation. The invention therefore provides methods of screening for compounds, e.g., small molecules, antibodies, siRNA, antisense molecules, and ribozyme, that are capable of modulating cell cycle regulation and cellular proliferation, e.g., either inhibiting or activating cellular proliferation. Therapeutic and diagnostic methods and reagents are also provided.

In one aspect of the invention, nucleic acids encoding LETM1 membrane receptors are provided. In another aspect, the present invention provides nucleic acids, such as probes, siRNA, antisense oligonucleotides, and ribozymes, that hybridize to a gene encoding LETM1. In another aspect, the invention provides expression vectors and host cells comprising LETM1-encoding nucleic acids. In another aspect, the present invention provides LETM1 protein, and antibodies thereto.

In another aspect, the present invention provides a method for identifying a compound that modulates cell cycle regulation and cellular proliferation, the method comprising the steps of: (i) contacting the compound with a LETM1 polypeptide; and (ii) determining the functional effect of the compound upon the LETM1 polypeptide.

In one embodiment, the functional effect is a physical effect or a chemical effect. In one embodiment, the polypeptide is expressed in a eukaryotic host cell. In another embodiment, the functional effect is determined by measuring receptor or signal transduction activity, e.g., increases in intracellular calcium or other signaling compounds.

In another aspect, the present invention provides a method of modulating cell cycle regulation and cellular proliferation in a subject, the method comprising the step of contacting the subject with an therapeutically effective amount of a compound identified using the methods described herein.

In one embodiment, the compounds identified using the assays of the invention are used to treat neuromuscular disease, cancer, cardiovascular disease, and psoriasis.

In another aspect, the present invention provides a method of detecting the presence of LETM1 nucleic acids and polypeptides in human tissue, the method comprising the steps of: (i) isolating a biological sample; (ii) contacting the biological sample with a LETM1-specific reagent that selectively associates with LETM1; and, (iii) detecting the level of LETM1-specific reagent that selectively associates with the sample.

In one embodiment, the human LETM1-specific reagent is selected from the group consisting of: human LETM1-specific antibodies, human LETM1 specific oligonucleotide primers, and human LETM1-nucleic acid probes.

BRIEF DESCRIPTION OF THE DRAWINGS

FIG. 1 provide exemplary wild type nucleotide (SEQ ID NO: 1) and amino acid (SEQ ID NO: 2) sequences for LETM1.

FIG. 2 provides data for cDNAs identified in a screen for inhibitors of cellular proliferation.

DETAILED DESCRIPTION OF THE INVENTION

Introduction

Figure 3:
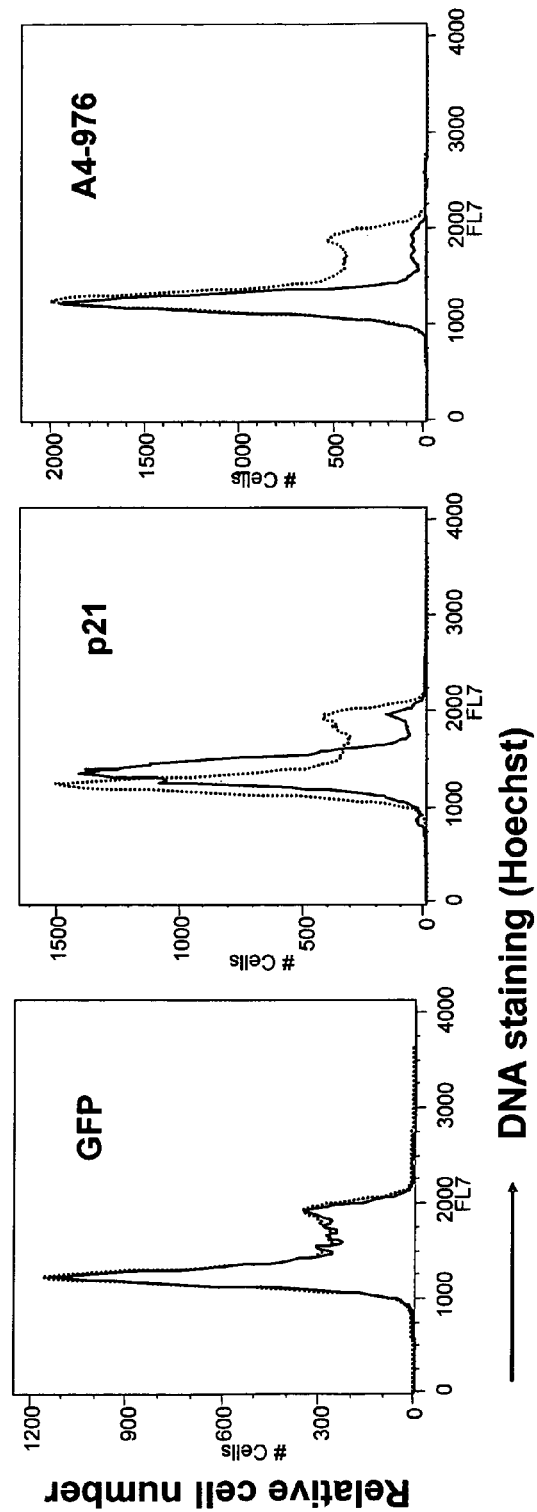
FIG. 3 demonstrates DNA transfer of phenotype for clone A4-976 (LETM1).

Here we report the identification and molecular characterization of a cell surface molecule, leucine zipper-EF-hand containing transmembrane protein 1 (LETM1), through a retroviral cDNA/peptide library-based functional screening using Tet-regulatable gene expression system. For the first time, LETM1 has been identified as a transmembrane protein involved in modulation of cell cycle regulation and cellular proliferation. LETM1 was identified from a functional genetic screen that selects for cells with cell cycle arrest. Clone A4-976 caused $G_0/G_1$ arrest and was found to encode LETM1, a membrane receptor (see, e.g., Endele et al., *Genomics* 60:218–225 (1999)). LETM-1 was originally identified as the gene that flanks the critical region of the wolf-hirschhorn syndrome (WHS), a chromosomal disorder characterized by a deletion at 4p16.3 and 4p monosomy resulting in facial dysmorphic features and neurological manifestations, e.g., severe pre- and post-natal growth retardation, severe mental retardation, developmental delay with microcephaly, "Greek warrior helmet," impairment of muscular tone, seizures, and B cell deficiency. LETM1 is deleted in most WHS patients and is localized to human chromosome 4p16.3. Translocations t(4;14(p 16.3;q3) are associated with multiple myeloma. The results provided herein demonstrate LETM-1 causes potent $G_0/G_1$ arrest in p53 independent and Rb dependent manor. Cell cycle regulation through LETM-1 also plays an important role in neuromuscular development.

LETM1 contains a leader sequence, RGD, a transmembrane region, a leucine zipper and two EF hands. Accession numbers AF061025 and NM__012318 (SEQ ID NO:1) provide an exemplary nucleotide sequence of wild type LETM1, and Accession numbers NP__036450 (SEQ ID NO:2) and AAD13138 provide exemplary amino acid sequences of wild type LETM1. Expression analysis provided herein shows that LETM1 is ubiquitously expressed in tumor cells. LETM1 is further over or underexpressed in tumor cells as compared to normal tissues.

LETM1 is a protein involved in tumor progression that therefore represents a drug target for compounds that suppress or activate cellular proliferation, or cause cell cycle arrest, or cause release from cell cycle arrest. Agents identified in these assays, including small molecule chemical compositions, antibodies, siRNA, antisense nucleic acids, and ribozymes, that modulate cell cycle regulation and cellular proliferation via modulation of LETM1 and LETM1 related signal transduction, can be used to treat diseases related to cellular proliferation. Such modulators are useful for treating cancers, such as melanoma, breast, ovarian, lung, gastrointestinal and colon, prostate, and leukemia and lymphomas, e.g., multiple myeloma. LETM1 is also associated with Wolf Hirschhorn syndrome (WHS) and therefore modulators of LETM1 should be useful for treating WHS. In addition, such modulators are useful for treating noncancerous disease states caused by pathologically proliferating cells such as thyroid hyperplasia (Grave's disease), psoriasis, benign prostatic hypertrophy, neurofibromas, atherosclerosis, restenosis, and other vasoproliferative disease.

Definitions

By "disorder associated with cellular proliferation" or "disease associated with cellular proliferation" herein is meant a disease state which is marked by either an excess or a deficit of cellular proliferation. Such disorders associated with increased cellular proliferation include, but are not limited to, cancer and non-cancerous pathological proliferation.

The terms "LETM1" or a nucleic acid encoding "LETM1" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by an LETM1 nucleic acid (Accession numbers AF061025 and NM__012318 or amino acid sequence of an LETM1 protein (Accession numbers NP__036450 and AAD13138); (2) bind to antibodies, e.g., polyclonal antibodies, raised against an immunogen comprising an amino acid sequence of an LETM1 protein (Accession numbers NP__036450 and AAD13138), and conservatively modified variants thereof; (3) specifically hybridize under stringent hybridization conditions to an anti-sense strand corresponding to a nucleic acid sequence encoding an LETM1 protein (Accession numbers AF061025 and NM—12318 and Accession numbers NP__036450 and AAD13138), and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to an LETM1 nucleic acid (Accession numbers AF061025 and NM__12318. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

"Membrane receptor activity," refers to signal transduction in response to extracellular stimuli and production of second messengers such as IP3, cAMP, and Ca2+ via stimulation of enzymes such as phospholipase C and adenylate cyclase. Such activity can be measured by examining increases in intracellular calcium using (Offermans & Simon, *J. Biol. Chem.* 270:15175–15180 (1995)). Receptor activity can be effectively measured by recording ligand-induced changes in $[Ca^{2+}]_i$ using fluorescent $Ca^{2+}$-indicator dyes and fluorometric imaging.

Such receptors have transmembrane, extracellular and cytoplasmic domains that can be structurally identified using methods known to those of skill in the art, such as sequence analysis programs that identify hydrophobic and hydrophilic domains (see, e.g., Kyte & Doolittle, *J. Mol. Biol.* 157: 105–132 (1982)). Such domains are useful for making chimeric proteins and for in vitro assays of the invention.

The phrase "functional effects" in the context of assays for testing compounds that modulate activity of an LETM1 protein includes the determination of a parameter that is indirectly or directly under the influence of an LETM1, e.g., a functional, physical, or chemical effect, such as the ability to increase or decrease cellular proliferation. It includes cell cycle arrest, the ability of cells to proliferate, and other characteristics of proliferating cells. "Functional effects" include in vitro, in vivo, and ex vivo activities.

By "determining the functional effect" is meant assaying for a compound that increases or decreases a parameter that is indirectly or directly under the influence of an LETM1 protein, e.g., functional, physical and chemical effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand binding activity; measuring cellular proliferation; measuring cell surface marker expression; measurement of changes in protein levels for LETM1-associated sequences; measurement of RNA stability; phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, calorimetric reactions, antibody binding, inducible markers, and ligand binding assays.

"Inhibitors", "activators", and "modulators" of LETM1 polynucleotide and polypeptide sequences are used to refer to activating, inhibitory, or modulating molecules identified using in vitro and in vivo assays of LETM1 polynucleotide and polypeptide sequences. Inhibitors are compounds that, e.g., bind to, partially or totally block activity, decrease, prevent, delay activation, inactivate, desensitize, or down regulate the activity or expression of LETM1 proteins, e.g., antagonists. "Activators" are compounds that increase, open, activate, facilitate, enhance activation, sensitize, agonize, or up regulate LETM1 protein activity. Inhibitors, activators, or modulators also include genetically modified versions of LETM1 proteins, e.g., versions with altered activity, as well as naturally occurring and synthetic ligands, antagonists, agonists, antibodies, siRNA, antisense molecules, ribozymes, small chemical molecules and the like. Such assays for inhibitors and activators include, e.g., expressing LETM1 protein in vitro, in cells, or cell membranes, applying putative modulator compounds, and then determining the functional effects on activity, as described above.

Samples or assays comprising LETM1 proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of LETM1 is achieved when the activity value relative to the control is about 80%, preferably 50%, more preferably 25-0%. Activation of LETM1 is achieved when the activity value relative to the control (untreated with activators) is 110%, more preferably 150%, more preferably 200–500% (i.e., two to five fold higher relative to the control), more preferably 1000–3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation cellular proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., FIG. 1, provided herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52): 35095–35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, extracellular domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15–50 nucleotides in length (e.g., each complementary sequence of the double stranded siRNA is 15–50 nucleotides in length, and the double stranded siRNA is about 15–50 base pairs in length, preferable about preferably about 20–30 base nucleotides, preferably about 20–25 nucleotides in length, e.g., 20, 21, 22, 23, 24, 25, 26, 27, 28, 29, or 30 nucleotides in length.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as following: 50% as formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec-2 min., an annealing phase lasting 30 sec.-2 min., and an extension phase of about 72° C. for 1–2 min. Protocols and guidelines for low and high stringency amplification reactions are provided, e.g., in Innis et al. (1990) *PCR Protocols, A Guide to Methods and Applications*, Academic Press, Inc. N.Y.).

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al "Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

For preparation of antibodies, e.g., recombinant, monoclonal, or polyclonal antibodies, many technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to LETM1 protein, polymorphic variants, alleles, orthologs, and conservatively modified variants, or splice variants, or portions thereof, can be selected to obtain only those polyclonal antibodies that are specifically immunoreactive with LETM1proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Isolation of Nucleic Acids Encoding LETM1

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

LETM1 nucleic acids, polymorphic variants, orthologs, and alleles that are substantially identical to an amino acid sequence the Accession numbers provided herein can be isolated using LETM1 nucleic acid probes and oligonucleotides under stringent hybridization conditions, by screening libraries. Alternatively, expression libraries can be used to clone LETM1 protein, polymorphic variants, orthologs, and alleles by detecting expressed homologs immunologically with antisera or purified antibodies made against human LETM1 or portions thereof.

To make a cDNA library, one should choose a source that is rich in LETM1 RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffinan, *Gene* 25:263–269 (1983); Sambrook et al., supra; Ausubel et al, supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating LETM1 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human LETM1 directly from mRNA, from cDNA, from genomic libraries or cDNA libraries. Degenerate oligonucleotides can be designed to amplify LETM1 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of LETM1 encoding mRNA in physiological samples, for nucleic acid sequencing, or for other purposes. Genes amplified by the PCR reaction can be purified from agarose gels and cloned into an appropriate vector.

Gene expression of LETM1 can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding LETM1 protein can be used with high density oligonucleotide array technology (e.g., GeneChip™) to identify LETM1 protein, orthologs, alleles, conservatively modified variants, and polymorphic variants in this invention. In the case where the homologs being identified are linked to modulation of cell cycle regulation, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

The gene for LETM1 is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding LETM1, one typically subclones LETM1 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the LETM1 protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the LETM1 encoding nucleic acid in host cells. A typical expression cassette thus contains a promoter operably linked to the nucleic acid sequence encoding LETM1 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, *Rous sarcoma* virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a LETM1 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of LETM1 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing LETM1.

After the expression vector is introduced into the cells, the transfected cells are cultured under conditions favoring expression of LETM1, which is recovered from the culture using standard techniques identified below.

Purification of LETM1 Polypeptides

Either naturally occurring or recombinant LETM1 can be purified for use in functional assays. Naturally occurring LETM1 can be purified, e.g., from human tissue. Recombinant LETM1 can be purified from any suitable expression system.

The LETM1 protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant LETM1 protein is being purified. For example, proteins having established molecular adhesion properties can be reversible fused to the LETM1 protein. With the appropriate ligand, LETM1 protein can be selectively adsorbed to a purification column and then freed from the column in a relatively pure form. The fused protein is then removed by enzymatic activity. Finally, LETM1 protein could be purified using immunoaffinity columns.

A. Purification of LETM1 From Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of LETM1 protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human LETM1 proteins are separated from other bacterial proteins by standard separation techniques, e.g., with Ni-NTA agarose resin.

Alternatively, it is possible to purify LETM1 protein from bacteria periplasm. After lysis of the bacteria, when the LETM1 protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques For Purifying LETM1 Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the LETM1 proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The LETM1proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Immunological Detection of LETM1 Polypeptides

In addition to the detection of LETM1 genes and gene expression using nucleic acid hybridization technology, one can also use immunoassays to detect LETM1 proteins of the invention. Such assays are useful for screening for modulators of LETM1 regulation of cellular proliferation, as well as for therapeutic and diagnostic applications. Immunoassays can be used to qualitatively or quantitatively analyze LETM1 proteins. A general overview of the applicable technology can be found in Harlow & Lane, *Antibodies: A Laboratory Manual* (1988).

Methods of producing polyclonal and monoclonal antibodies that react specifically with the LETM1 proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of LETM1 protein may be used to produce antibodies specifically reactive with LETM1 protein. For example, recombinant LETM1 protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-LETM1 proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular LETM1 ortholog, such as human LETM1, can also be made, by subtracting out other cross-reacting orthologs from a species such as a non-human mammal.

Once the specific antibodies against LETM1 protein are available, the protein can be detected by a variety of immunoassay methods. In addition, the antibody can be used therapeutically as a LETM1 modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

Assays For Modulators Of LETM1 Protein

A. Assays

Modulation of cell cycle regulation can be assessed using a variety of in vitro and in vivo assays, as described above, and, such assays can be used to test for inhibitors and activators of LETM1 protein. Such modulators of LETM1 protein, which is involved in cell cycle regulation, are useful for treating disorders related to abnormal cellular proliferation, such as cancer. Modulators of LETM1 protein are tested using either recombinant or naturally occurring, preferably human LETM1.

Preferably, the LETM1 protein will have the sequence as provided in an Accession number, described herein. Alternatively, the LETM1 protein of the assay will be derived from a eukaryote and include an amino acid subsequence having substantial amino acid sequence identity to the Accession numbers described herein. Generally, the amino acid sequence identity will be at least 60%, preferably at least 65%, 70%, 75%, 80%, 85%, or 90%, most preferably at least 95%.

Measurement of a cell cycle arrest or release, or loss-of-proliferation phenotype on LETM1 protein or cell expressing LETM1 protein, either recombinant or naturally occurring, can be performed using a variety of assays, in vitro, in vivo, and ex vivo. A suitable physiological change that affects activity or binding can be used to assess the influence of a test compound on the polypeptide of this invention. When the functional effects are determined using intact cells or animals, one can also measure a variety of effects such as, increases or decreases in cellular proliferation, or in the case of signal transduction, hormone release, transcriptional changes to both known and uncharacterized genetic markers (e.g., northern blots), changes in cell metabolism such as cell growth or pH changes, and changes in intracellular second messengers such as cGMP.

In a preferred embodiment, LETM1 modulators are assayed by screening for cell cycle arrest, as described in Example 1. Cellular proliferation assays, such as $^3$H-thymidine assays, can also be used to assay for cell cycle modulation, and are well known to those of skill in the art.

Assays to identify compounds with modulating activity can be performed in vitro. For example, LETM1 protein is first contacted with a potential modulator and incubated for a suitable amount of time, e.g., from 0.5 to 48 hours. In one embodiment, LETM1 polypeptide levels are determined in vitro by measuring the level of protein or mRNA. The level of LETM1 protein or proteins related to LETM1 signal transduction are measured using immunoassays such as western blotting, ELISA and the like with an antibody that selectively binds to the LETM1 polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using an LETM1 protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)). The reporter construct is typically transfected into a cell. After treatment with a potential modulator, the amount of reporter gene transcription, translation, or activity is measured according to standard techniques known to those of skill in the art.

An activated or inhibited LETM1 receptor will alter the properties of downstream target enzymes, channels, and other effector proteins. Downstream consequences can be examined such as generation of diacyl glycerol and IP3 by phospholipase C, and in turn, for calcium mobilization by IP3. Receptor activation typically initiates subsequent intracellular events, e.g., increases in second messengers such as IP3, which releases intracellular stores of calcium ions. Thus, a change in cytoplasmic calcium ion levels, or a change in second messenger levels such as IP3 can be used to assess receptor function. Cells expressing such receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay.

In one embodiment, the changes in intracellular cAMP or cGMP can be measured using immunoassays. The method described in Offermanns & Simon, *J. Biol. Chem.* 270: 15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

B. Modulators

The compounds tested as modulators of LETM1 protein can be any small chemical compound, or a biological entity, such as a protein, e.g., an antibody, a sugar, a nucleic acid, e.g., an antisense oligonucleotide, siRNA, or a ribozyme, or a lipid. Alternatively, modulators can be genetically altered versions of an LETM1 protein. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing the LETM1 protein is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds are possible using the integrated systems of the invention.

C. Solid State and Soluble High Throughput Assays

In one embodiment the invention provides soluble assays using a LETM1protein, or a cell or tissue expressing an LETM1protein, either naturally occurring or recombinant. In another embodiment, the invention provides solid phase based in vitro assays in a high throughput format, where the LETM1 protein is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

The protein of interest, or a cell or membrane comprising the protein of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Cellular Transfection and Gene Therapy

The present invention provides the nucleic acids of LETM1 protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a LETM1 protein of the present invention, thereby mitigating the effects of absent, partial inactivation, or abnormal expression of an LETM1 gene, particularly as it relates to cell cycle regulation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175(1993); Miller, *Nature* 357: 455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the LETM1 protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of LETM1 as a Cell Cycle Regulator

Figure 4:
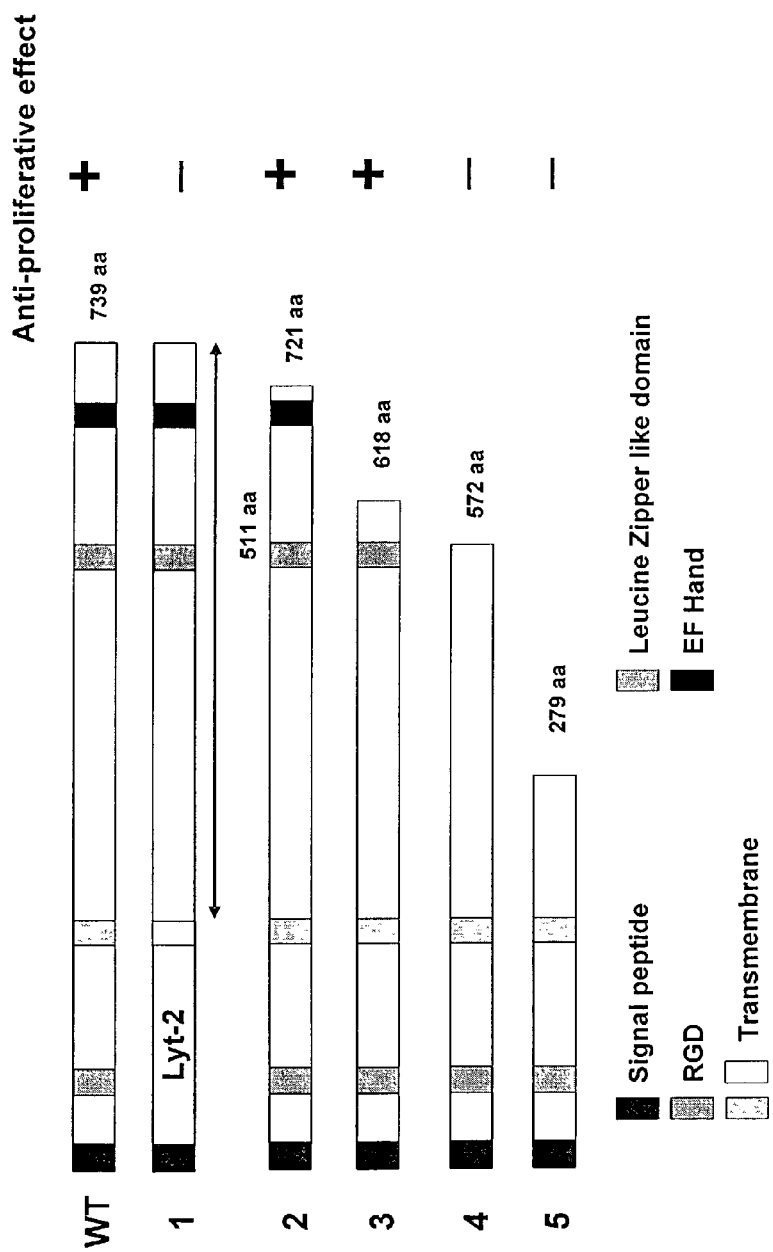
FIG. 4 shows analysis of LETM1 functional domains.
Figure 5:
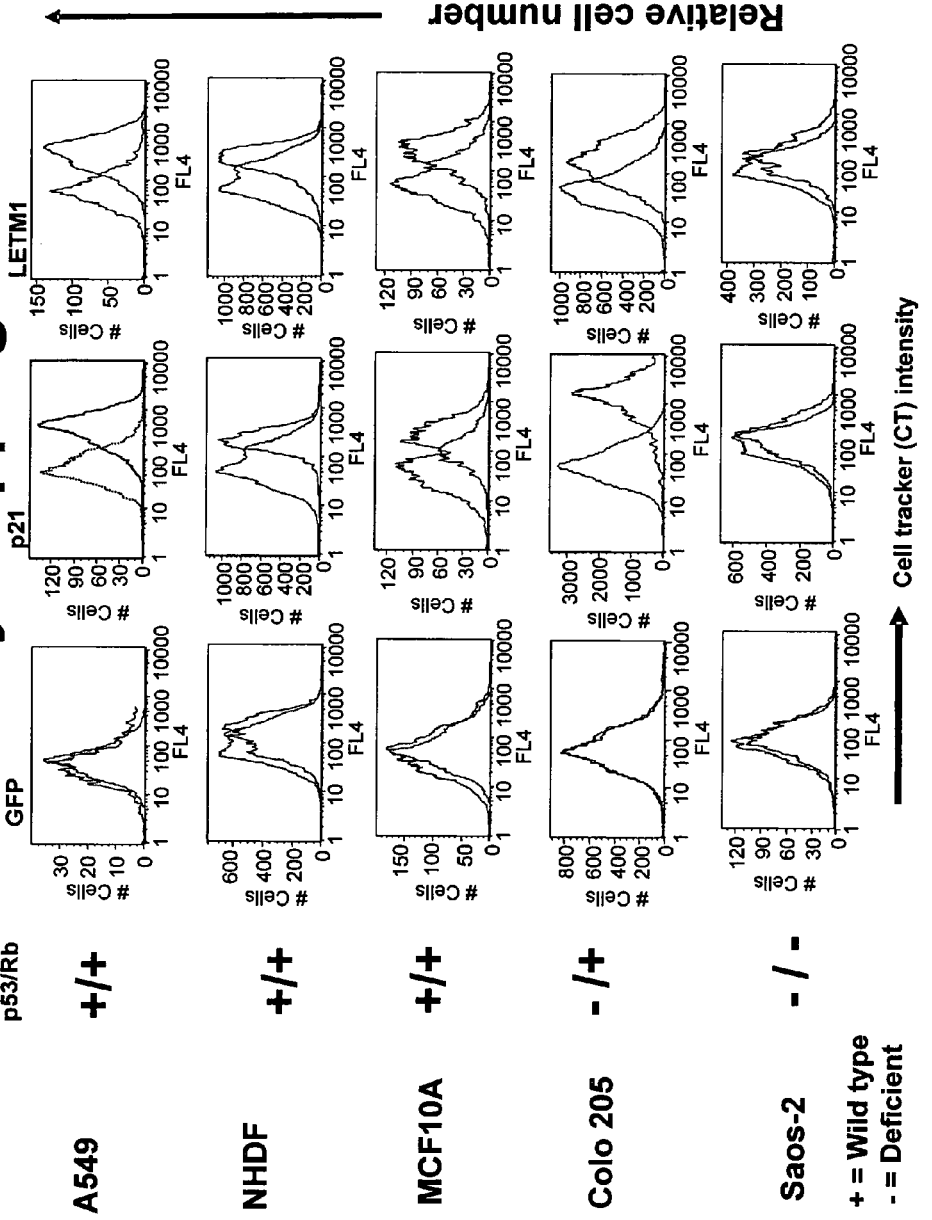
FIG. 5 provides functional pathway mapping for LETM1.
Figure 6:
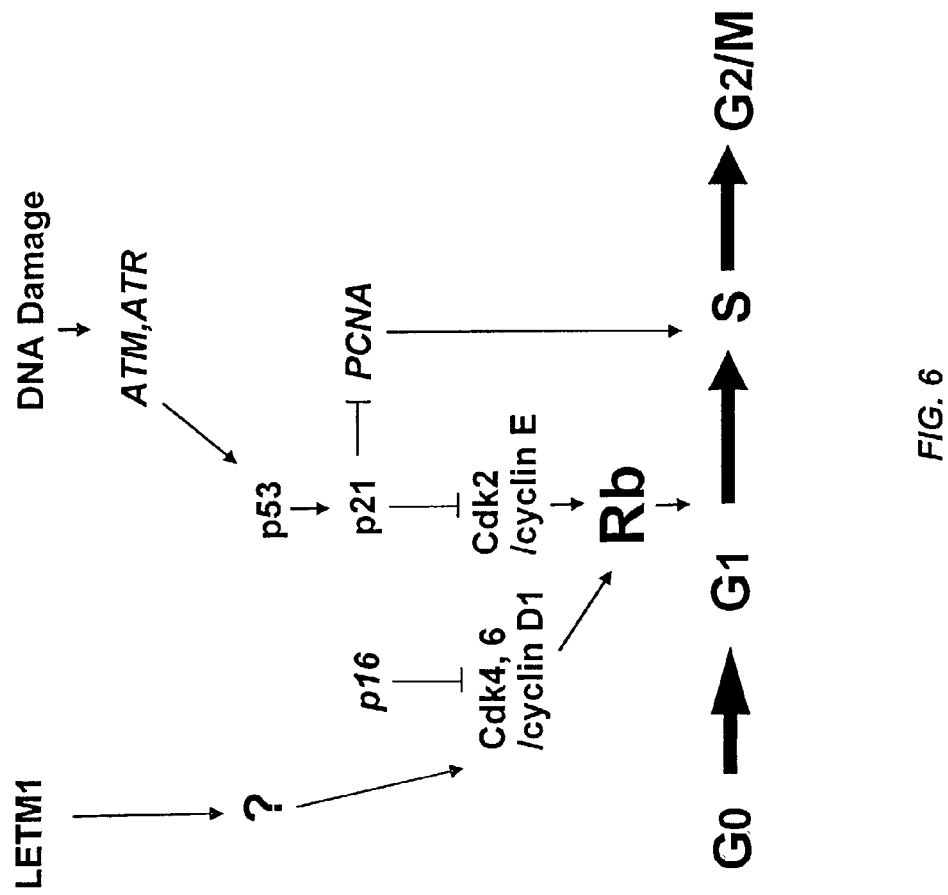
FIG. 6 provides a schematic pathway showing that LETM1 induces $G_0/G_1$ arrest through Rb (retinoblastoma protein).
Figure 7:
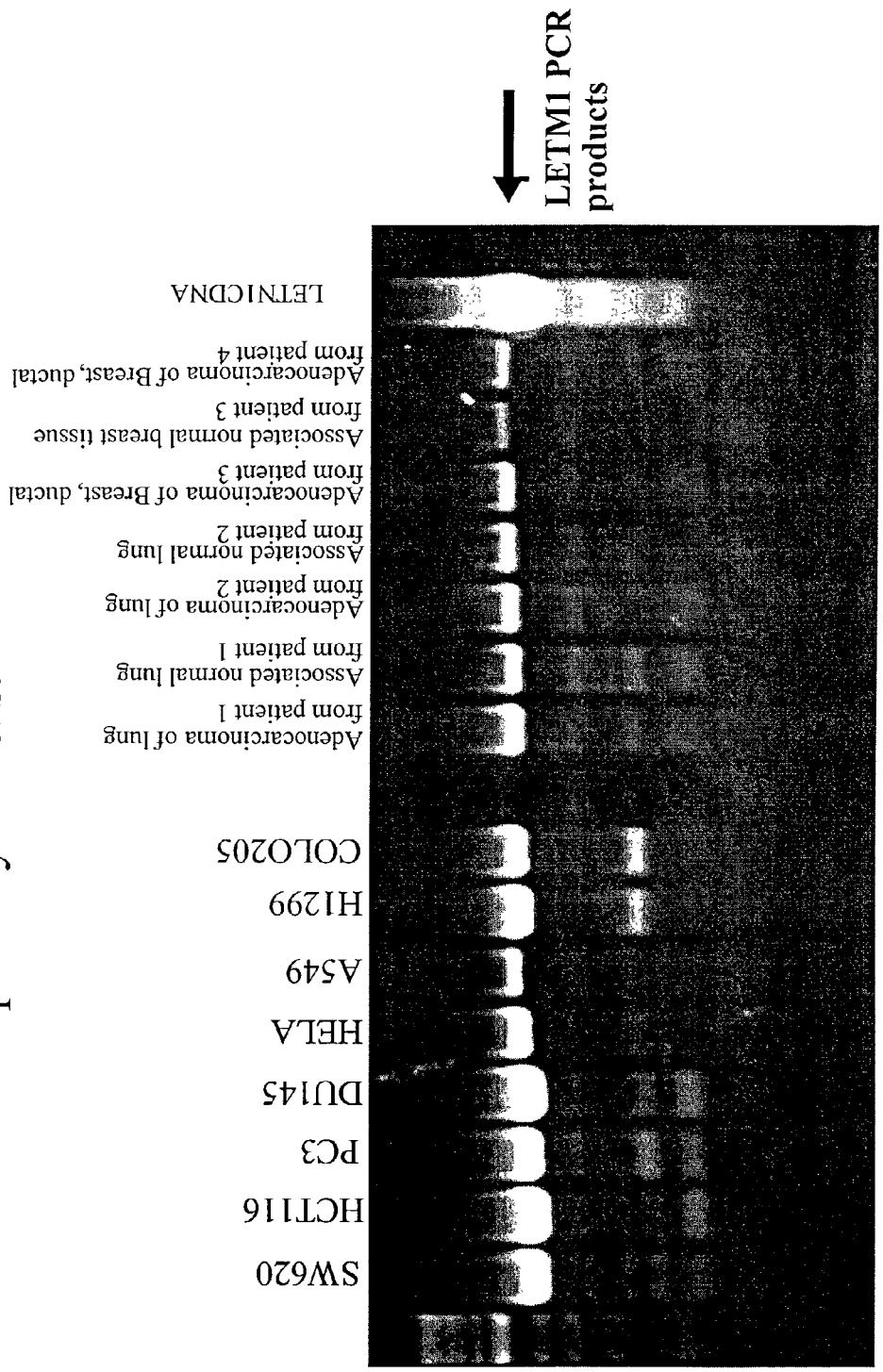
FIG. 7 shows RT-PCR analysis of LETM1 expression in several tumor cell lines and primary tumor samples.
Figure 8:
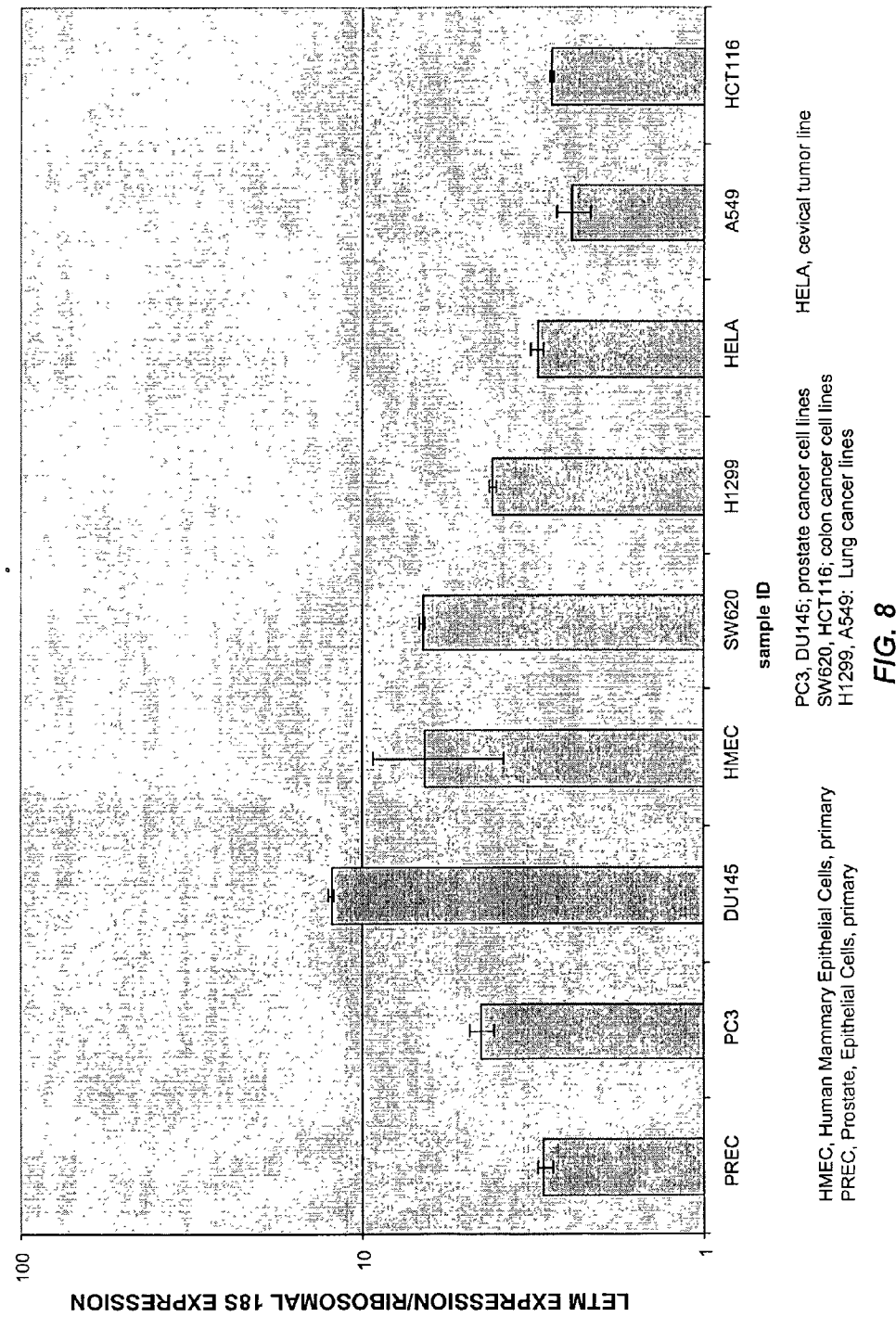
FIG. 8 shows Taqman analysis of LETM1 expression in several tumor cell lines and primary tumor samples. Prostate tumor cells (DU145 and PC3) showed increased LETM1 levels are compared to primary prostate epithelial cells. LETM1 levels are high in primary breast cells.
Figure 9:
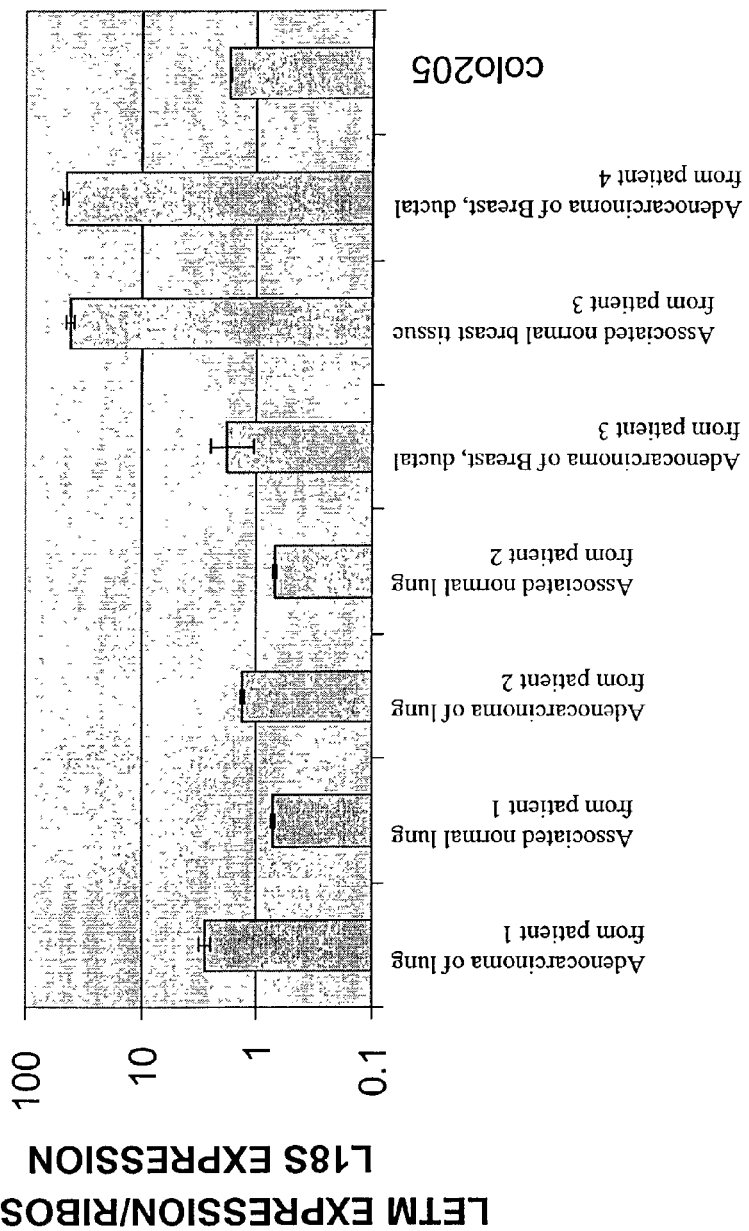
FIG. 9 shows that LETM1 overexpression in lung tumor cells relative to associated normal tissues. LETM1 is down-regulated in breast tumors.

For isolation of cDNAs that cause cell cycle arrest, A549.tTA cells are infected with a cDNA library in a Tet-inducible retroviral vector. Cycling cells are infected with retrovirus encoding DT-α and killed. CT bright cells are sorted as single cells onto 96/384 well plates. The clones are expanded in the presence of Dox. Clones that fail to grow in the absence of Dox are isolated and rescued by RT-PCR. Clones are evaluated by splitting the cells into two wells, culturing the cells plus and minus Dox for 5–7 days, and then adding AlamarBlue and measuring fluorescence. The growth ratio is calculated as the fluorescence intensity of cells with Dox over the fluorescence intensity of cells without Dox (see FIG. 2). Growth arrest for clone A4-976 was inducible using Dox (Dox+, cDNA off, proliferation; Dox–, cDNA on, growth arrest). Cell tracker assays were also used to measure inducible growth arrest. Phenotype transfer of cell cycle arrest phenotype was demonstrated with DNA staining (Hoechst) (FIG. 3). Clone A4-976 encodes wild-type LETM1 (739 amino acids). Deletion analysis showed functional domains of LETM1 (FIG. 4). Functional pathway mapping was performed for LETM1 (FIG. 5). LETM1 was shown to induce $G_0/G_1$ arrest through Rb (FIG. 6).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that activates or inhibits cellular proliferation, the method comprising the steps of:
   (i) contacting the compound with a LETM1 polypeptide, the polypeptide encoded by a nucleic acid that hybridizes under stringent conditions to a nucleic acid encoding a polypeptide having the amino acid sequence of SEQ ID NO:2, wherein the stringent conditions comprise 50% formamide, 5×SSC, and 1% SDS, incubating at 42° C., or in 5× SSC, 1% SDS, incubating at 65° C., with wash in 0.2×SSC, and 0.1% SDS at 65° C.; and (ii) determining the functional effect of the compound upon the LETM1 polypeptide.

2. The method of claim 1, wherein the functional effect is measured in vitro.

3. The method of claim 2, wherein the functional effect is a physical effect.

4. The method of claim 3, wherein the functional effect is determined by measuring ligand binding to the polypeptide.

5. The method of claim 2, wherein the functional effect is a chemical effect.

6. The method of claim 1, wherein the polypeptide is expressed in a eukaryotic host cell or cell membrane.

7. The method of claim 6, wherein the functional effect is a physical effect.

8. The method of claim 7, wherein the functional effect is determined by measuring ligand binding to the polypeptide.

9. The method of claim 6, wherein the functional effect is a chemical or phenotypic effect.

10. The method of claim 9, wherein the chemical or phenotypic effect is determined by measuring cellular proliferation.

11. The method of claim 10, wherein the cellular proliferation is measured by assaying for DNA synthesis or fluorescent marker dilution.

12. The method of claim 11, wherein DNA synthesis is measured by $^3$H thymidine incorporation, BrdU incorporation, or Hoechst staining.

13. The method of claim 11, wherein the fluorescent marker is selected from the group consisting of a cell tracker dye or green fluorescent protein.

14. The method of claim 1, wherein the compound inhibits cancer cell proliferation.

15. The method of claim 6, wherein the host cell is a cancer cell.

16. The method of claim 15, wherein the cancer cell is a breast, prostate, colon, or lung cancer cell.

17. The method of claim 15, wherein the cancer cell is a transformed cell line.

18. The method of claim 15, wherein the cancer cell is p53 null or mutant.

19. The method of claim 15, wherein the cancer cell is p53 wild-type.

20. The method of claim 1, wherein the polypeptide is recombinant.

21. The method of claim 1, wherein the polypeptide is encoded by a nucleic acid comprising a sequence of SEQ ID NO: 1.

22. The method of claim 1, wherein the compound is an antibody.

23. The method of claim 1, wherein the compound is an antisense molecule.

24. The method of claim 1, wherein the compound is an siRNA molecule.

25. The method of claim 1, wherein the compound is a small organic molecule.

26. The method of claim 1, wherein the compound is a peptide.

27. The method of claim 1, wherein said LETM1 polypeptide comprises a transmembrane sequence.

28. A method for identifying a compound that inhibits cellular proliferation, the method comprising the steps of:

(i) contacting the compound with a LETM1 polypeptide, the polypeptide encoded by a nucleic acid that hybridizes under stringent conditions to a nucleic acid encoding a polypeptide having the amino acid sequence of SEQ ID NO:2, wherein the stringent conditions comprise 50% formamide, 5×SSC, and 1% SDS, incubating at 42° C., or in 5× SSC, 1% SDS, incubating at 65° C., with wash in 0.2×SSC, and 0.1% SDS at 65° C.; and (ii) determining the functional effect of the compound upon the LETM1 polypeptide.

29. The method of claim 28, wherein said LETM1 polypeptide causes $G_0/G_1$ cell cycle arrest in a p53 independent and a Rb dependent manner.

* * * * *